United States Patent [19]

Chu et al.

[11] 4,347,395

[45] Aug. 31, 1982

[54] CONVERSION OF PARAFFINIC HYDROCARBONS TO AROMATICS OVER ZEOLITE CATALYSTS

[75] Inventors: Yung F. Chu; Arthur W. Chester, both of Cherry Hill, N.J.

[73] Assignee: Mobil Oil Corporation, New York, N.Y.

[21] Appl. No.: 253,132

[22] Filed: Apr. 13, 1981

[51] Int. Cl.$^3$ .................... C07C 12/02; C07C 12/42; C07C 12/46
[52] U.S. Cl. ............................... 585/420; 585/415; 585/417; 585/419
[58] Field of Search ............... 585/417, 415, 419, 420

[56] References Cited

U.S. PATENT DOCUMENTS

| | | | |
|---|---|---|---|
| 3,760,024 | 9/1973 | Cattanach | 585/415 |
| 3,775,501 | 11/1973 | Kaeding et al. | 260/673 |
| 3,827,867 | 8/1974 | Heinemann et al. | 585/415 X |
| 3,845,150 | 10/1974 | Yan et al. | 585/415 X |
| 3,894,103 | 7/1975 | Chang et al. | 585/415 X |
| 3,894,104 | 7/1975 | Chang et al. | 585/415 X |
| 4,067,920 | 1/1978 | Kaeding | 585/415 X |
| 4,120,910 | 10/1978 | Chu | 260/673 |
| 4,260,839 | 4/1981 | Chen et al. | 585/415 X |

*Primary Examiner*—Paul F. Shaver
*Attorney, Agent, or Firm*—Charles A. Huggett; Michael G. Gilman; Van D. Harrison, Jr.

[57] ABSTRACT

Paraffinic hydrocarbons of 2 to 16 carbon atoms are converted to aromatic in the presence of oxygen and a zeolite catalyst incorporating oxidative dehydrogenative metal or metal oxide components

19 Claims, No Drawings

CONVERSION OF PARAFFINIC HYDROCARBONS TO AROMATICS OVER ZEOLITE CATALYSTS

BACKGROUND OF THE INVENTION

1. Field of the Invention

This invention relates to the production of aromatics from gaseous paraffinic hydrocarbons. More particularly this invention is concerned with the production of such aromatics from hydrocarbons contacted with a zeolite.

2. Description of the Prior Art

U.S. Pat. No. 3,775,501 discloses the production of aromatics from a hydrocarbon feed stock comprising a mixture of air or oxygen and a hydrocarbon having from 2 to about 16 carbon atoms by passing the mixture over a catalyst comprising a crystalline aluminosilicate having uniform pore openings of greater than 5 angstrom units. Representative crystalline aluminosilicate zeolites which can be used include zeolite Beta, TEA mordenite, ZSM-12 and a family of zeolites referred to as ZSM-5 type which includes as members ZSM-5, ZSM-8 and ZSM-11.

U.S. Pat. No. 4,120,910 discloses the conversion of gaseous paraffinic feedstocks containing ethane to liquid aromatics by contacting the gaseous feed, in the absence of added air or oxygen, under suitable conversion conditions, with a zeolite catalyst having incorporated therein a minor amount of a metal selected from Groups VIII, IIB and IB of the periodic table. Such metals include zinc, copper or platinum and preferably a zinc-copper mixture.

SUMMARY OF THE INVENTION

Briefly stated, this invention comprises a process for producing aromatic compounds which comprises contacting a gaseous hydrocarbon feed stock containing a high percentage of paraffinic hydrocarbons of 2 to 16 carbon atoms with oxygen or air and with a ZSM-5 type crystalline zeolite catalyst combined with a metal or metal oxide oxidative dehydrogenation component whereby at least a portion of the hydrocarbons present in the gaseous feed is converted to liquid aromatic compounds.

DESCRIPTION OF THE INVENTION

Accordingly, the present invention is a process for producing aromatic hydrocarbons comprising contacting a gaseous paraffinic feed containing a high percentage of hydrocarbons of 2 to 16 carbon atoms with oxygen or an oxygen-containing gas and with a crystalline zeolite catalyst of the ZSM-5 type combined with a minor amount of a metal or metal oxide oxidative dehydrogenation component.

The crystalline zeolites utilized herein are members of a novel class of zeolitic materials which exhibit unusual properties. Although these zeolites have unusually low alumina contents, i.e. high silica to alumina mole ratios, they are very active even when the silica to alumina mole ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conductive to long times on stream between regenerations by burning carbonaceous deposits with oxygen-containing gas such as air.

An important characteristic of the crystal structure of this novel class of zeolites is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon (or aluminum, etc.) atoms at the centers of the tetrahedra.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with silica to alumina mole ratios of at least 12 are useful, it is preferred in some instances to use zeolites having substantially higher silica/alumina ratios, e.g. 1600 and above. In addition, zeolites as otherwise characterized herein but which are substantially free of aluminum, that is zeolites having silica to alumina mole ratios of up to infinity, are found to be useful and even preferable in some instances. Such "high silica" or "highly siliceous" zeolites are intended to be included within this description. Also included within this definition are substantially pure silica analogs of the useful zeolites described herein, that is to say those zeolites having no measurable amount of aluminum (silica to alumina mole ratio of infinity) but which otherwise embody the characteristics disclosed.

The novel class of zeolites, after activation, acquire an intracrystalline sorption capacity for normal hexane which is greater than that for water, i.e. they exhibit "hydrophobic" properties. This hydrophobic character can be used to advantage in some applications.

The novel class of zeolites useful herein have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons and, therefore, it is not the present intention to entirely judge the usefulness of a particular zeolite solely from theoretical structural considerations.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

While the above experimental procedure will enable one to achieve the desired overall conversion of 10 to 60% for most zeolite samples and represents preferred conditions, it may occasionally be necessary to use somewhat more severe conditions for samples of very low activity, such as those having an exceptionally high silica to alumina mole ratio. In those instances, a temperature of up to about 540° C. and a liquid hourly space velocity of less than one, such as 0.1 or less, can be employed in order to achieve a minimum total conversion of about 10%.

The "Constraint Index" is calculated as follows:

$$\text{Constraint Index} = \frac{\log_{10} (\text{fraction of hexane remaining})}{\log_{10} (\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (CI) values for some typical materials are:

|  | C.I. |
|---|---|
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| ZSM-48 | 3.4 |
| TMA Offretite | 3.7 |
| Clinoptilolite | 3.4 |
| Beta | 0.6 |
| H-Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the constraint index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined novel class of highly siliceous zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value within the range of 1 to 12. Thus, it should be understood that the Constraint Index value as used herein is an inclusive rather than an exclusive value. That is, a crystalline zeolite when identified by any combination of conditions within the testing definition set forth herein as having a Constraint Index in the range of 1 to 12 is intended to be included in the instant novel zeolite definition whether or not the same identical zeolite, when tested under other of the defined conditions, may give a Constraint Index value outside of the range of 1 to 12.

The novel class of zeolites defined herein is exemplified by ZSM-5, ZSM-11, ZSM-12, ZSM-23, ZSM-35, ZSM-38, ZSM-48, and other similar materials.

ZSM-5 is described in greater detail in U.S. Pat. No. 3,702,886 and Re 29,948. The entire descriptions contained within those patents, particularly the X-ray diffraction pattern of therein disclosed ZSM-5, are incorporated herein by reference.

ZSM-11 is described in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-23 is described in U.S. Pat. No. 4,076,842. The entire content thereof, particularly the specification of the X-ray diffraction pattern of the disclosed zeolite, is incorporated herein by reference.

ZSM-35 is described in U.S. Pat. No. 4,016,245. The description of that zeolite, and particularly the X-ray diffraction pattern thereof, is incorporated herein by reference.

ZSM-38 is more particularly described in U.S. Pat. No. 4,046,859. The description of that zeolite, and particularly the specified X-ray diffraction pattern thereof, is incorporated herein by reference.

ZSM-48 can be identified, in terms of moles of anhydrous oxides per 100 moles of silica, as follows:

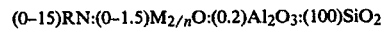

$$(0-15)RN:(0-1.5)M_{2/n}O:(0.2)Al_2O_3:(100)SiO_2$$

wherein:
M is at least one cation having a valence n; and

RN is a $C_1$-$C_{20}$ organic compound having at least one amine functional group of $pK_a \geq 7$.

It is recognized that, particularly when the composition contains tetrahedral framework aluminum, a fraction of the amine functional groups may be protonated. The doubly protonated form, in conventional notation, would be $(RNH)_2O$ and is equivalent in stoichiometry to $2\ RN + H_2O$.

The characteristic X-ray diffraction pattern of the synthetic zeolite ZSM-48 has the following significant lines:

| Characteristic Lines of ZSM-48 | |
|---|---|
| d (Angstroms) | Relative Intensity |
| 11.9 | W-S |
| 10.2 | W |
| 7.2 | W |
| 5.9 | W |
| 4.2 | VS |
| 3.9 | VS |
| 3.6 | W |
| 2.85 | W |

These values were determined by standard techniques. The radiation was the K-alpha doublet of copper, and a scintillation counter spectrometer with a strip chart pen recorder was used. The peak heights, I, and the positions as a function of 2 times theta, where theta is the Bragg angle, were read from the spectrometer chart. From these, the relative intensities, $100\ I/I_o$, where $I_o$ is the intensity of the strongest line or peak, and d (obs.), the interplanar spacing in angstroms, corresponding to the recorded lines, were calculated. In the foregoing table the relative intensities are given in terms of the symbols W=weak, VS=very strong and W-S=weak-to-strong. Ion exchange of the sodium ion with cations reveals substantially the same pattern with some minor shifts in interplanar spacing and variation in relative intensity. Other minor variations can occur depending on the silicon to aluminum ratio of the particular sample, as well as if it has been subjected to thermal treatment.

The ZSM-48 can be prepared from a reaction mixture containing a source of silica, water, RN, an alkali metal oxide (e.g. sodium) and optionally alumina. The reaction mixture should have a composition, in terms of mole ratios of oxides, falling within the following ranges:

| REACTANTS | | BROAD | PREFERRED |
|---|---|---|---|
| $Al_2O_3/SiO_2$ | = | 0 to 0.02 | 0 to 0.01 |
| $Na/SiO_2$ | = | 0 to 2 | 0.1 to 1.0 |
| $RN/SiO_2$ | = | 0.01 to 2.0 | 0.05 to 1.0 |
| $OH^-/SiO_2$ | = | 0 to 0.25 | 0 to 0.1 |
| $H_2O/SiO_2$ | = | 10 to 100 | 20 to 70 |
| $H^+$(added)$SiO_2$ | = | 0 to 0.2 | 0 to 0.05 | wherein RN is a $C_1$-$C_{20}$ organic compound having amine functional group of $pK_a \geq 7$. The mixture is maintained at 80°–250° C. until crystals of the material are formed. $H^+$ (added) is moles acid added in excess of the moles of hydroxide added. In calculating $H^+$ (added) and OH values, the term acid ($H^+$) includes both hydronium ion, whether free or coordinated, and aluminum. Thus aluminum sulfate, for example, would be considered a mixture of aluminum oxide, sulfuric acid, and water. An amine hydrochloride would be a mixture of amine and HCl. In preparing the highly siliceous form of ZSM-48 no alumina is added. Thus, the only aluminum present occurs as an impurity in the reactants.

Preferably, crystallization is carried out under pressure in an autoclave or static bomb reactor, at 80° C. to 250° C. Thereafter, the crystals are separated from the liquid and recovered. The composition can be prepared utilizing materials which supply the appropriate oxide. Such compositions include sodium silicate, silica hydrosol, silica gel, silicic acid, RN, sodium hydroxide, sodium chloride, aluminum sulfate, sodium aluminate, aluminum oxide, or aluminum itself. RN is a $C_1$-$C_{20}$ organic compound containing at least one amine functional group of $pK_a \geq 7$, as defined above, and includes such compounds as $C_3$-$C_{18}$ primary, secondary, and tertiary amines, cyclic amine (such as piperdine, pyrrolidine and piperazine), and polyamines such as $NH_2$—$C_nH_{2n}$—$NH_2$ wherein n is 4–12.

The original cations can be subsequently replaced, at least in part, by calcination and/or ion exchange with another cation. Thus, the original cations are exchanged into a hydrogen or hydrogen ion precursor form or a form in which the original cation has been replaced by a metal of Groups II through VIII of the Periodic Table. Thus, for example, it is contemplated to exchange the original cations with ammonium ions or with hydronium ions. Catalytically active forms of these would include, in particular, hydrogen, rare earth metals, aluminum, manganese and other metals of Groups II and VIII of the Periodic Table.

ZSM-48 is more particularly described in the pending U.S. application filed Nov. 18, 1980, (serial number unknown at this date) which is a continuation of application Ser. No. 64,703, filed Aug. 8, 1979, the entire contents of which are incorporated herein by reference.

It is to be understood that by incorporating by reference the foregoing patents and application to describe examples of specific members of the novel class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation of the identified patents should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are substantially catalytically inactive, possibly because the intra-crystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-12, ZSM-23, ZSM-35, ZSM-38 and ZSM-48, with ZSM-5 being particularly preferred.

In a preferred aspect of this invention, the zeolites hereof are selected as those providing among other things a crystal framework density, in the dry hydrogen form, of not less than about 1.6 grams per cubic centimeter. It has been found that zeolites which satisfy all three of the discussed criteria are most desired for several reasons. When hydrocarbon products or by-products are catalytically formed, for example, such zeolites tend to maximize the production of gasoline boiling range hydrocarbon products. Therefore, the preferred zeolites useful with respect to this invention are those having a Constraint Index as defined above of about 1 to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article Zeolite Structure by W. M. Meier. This paper, the entire contents of which are incorporated herein by reference, is included in Proceedings of the Conference on Molecular Sieves, (London, April 1967) published by the Society of Chemical Industry, London, 1968.

When the crystal structure is unknown, the crystal framework density may be determined by classical pycnometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

|  | Void Volume | Framework Density |
| --- | --- | --- |
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

In practicing a particularly desired chemical conversion process, it may be useful to incorporate the above-described crystalline zeolite with a matrix comprising another material resistant to the temperature and other conditions employed in the process. Such matrix material is useful as a binder and imparts greater resistance to the catalyst for the severe temperature, pressure and reactant feed stream velocity conditions encountered in many cracking processes.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

The metal or metal oxide oxidative dehydrogenation component which can be used in the process of this invention include iron oxides, preferably promoted with an alkali metal salt such as sodium carbonate and activated by being heated with steam for several hours at the temperature of the oxidative dehydrogenation process. A preferred catalyst of this type is one which is 2% potassium oxide, 5% chromium oxide and 93% ferric oxide and which has been activated by heating with steam at 1100° C. for two hours. Catalysts of this type are disclosed in U.S. Pat. No. 3,502,737.

Another catalyst which can be used is iron ferrites modified with an oxide of cerium, zinc, manganese or lead, and ferrites of barium modified, with the exception of cerium, with one of the aforementioned oxides. These catalyst compositions are discussed in U.S. Pat. No. 3,931,351. A zinc ferrite oxidative dehydrogenation catalyst is disclosed in U.S. Pat. No. 3,937,748. U.S. Pat. No. 4,108,919 discloses an oxidative dehydrogenation catalyst for dehydrogenating olefins to diolefins comprising a mixture of cobalt and molybdenum in combination with oxygen and/or zinc and molybdenum in combination with oxygen which is activated with chromium in combination with oxygen. U.S. Pat. No. 4,131,631 discloses the use of an oxidative dehydrogenation catalyst containing the oxide of cobalt and molybdenum, for dehydrogenating paraffins of from 3 to 6 carbon atoms. Optionally, an oxide or oxides of one or more of the elements selected from the group consisting of phosphorous and metals of Groups IA, IIA, VIB and VIII of the periodic table can be incorporated into the catalyst with the cobalt and molybdenum. The disclosures of U.S. Pat. Nos. 3,502,737; 3,931,351; 3,937,748; 4,108,919; and 4,131,631 are incorporated herein by reference.

The metal or metal oxide oxidative dehydrogenation component most preferred and believed at this time to be the best mode is either a combination of the oxides of chromium, molybdenum and phosphorous or the oxides of niobium, vanadium and molybdenum. These are demonstrated in the examples.

The manner in which the ZSM-5 type crystalline zeolite is utilized with the metal or metal oxide oxidative dehydrogenation component can be varied. The crystalline zeolite and metal or metal oxide component can be maintained in separate zones so that the gaseous paraffinic feed and air or oxygen streams are introduced first into a zone containing the metal or metal oxide. The effluent stream can then be flowed through a separate zone containing the crystalline zeolite. In this arrangement it is preferred to combine the zeolite with a porous matrix material as hereinabove described. It is also desirable to support the metal or metal oxide component on a suitable porous nonreactive material such as alumina or silica. Alternatively the air or oxygen and the hydrocarbon stream can be mixed prior to entering the first zone of metal or metal oxide catalyst.

In an alternate scheme the metal or metal oxide dehydrogenative component supported on a non reactive porous material and the crystalline zeolite in a porous matrix can be physically mixed and maintained in a single zone.

In still another variation the zeolite, or the porous matrix, or the composite mixture of the two can be ion exchanged or at least partially impregnated with the metal or metal oxide dehydrogenative component.

The process of this invention is conducted so that the gaseous hydrocarbon feed consisting primarily of paraffin of 2 to 16 carbon atoms and oxygen or an oxygen-containing gas, such as air, are contacted with the crystalline zeolite catalyst and hydrogenative metal component at a temperature of 450° C. to 650° C., a pressure of $1.01 \times 10^5$ to $42.38 \times 10^5$ pascal (0 to 600 psig), and a weight hourly space velocity ($C_2$ to $C_{16}$ hydrocarbons zeolite-porous matrix composite) of 0.1 and 10. A mole ratio of oxygen to $C_2$-$C_{16}$ hydrocarbons of between 0.1 and 1 can be used. More preferred conditions are a temperature of 500° C. to 600° C., pressure of $1.01 \times 10^5$ to $21.69 \times 10^5$ pascal (0 to 300 psig), a WHSV of 0.2 to 5 and a mole ratio of 0.1 to 0.5 of oxygen to $C_2$-$C_{16}$ hydrocarbons to oxygen.

The effluent from the reaction zone or zones is separated and fractionated to remove the desired aromatic compounds. The remaining materials can be further fractionated and recycled to the process if such is desired.

EXAMPLE

The catalyst compositions shown in Table 1 were prepared as follows:

Catalyst A was prepared by dissolving two grams of ammonium molybdate, $(NH_4)_2MO_4$, 0.24 grams of phosphoric acid, $(H_3PO_4)$, and 4.1 grams of chromic nitrate, $Cr(NO_3)_2.9H_2O$ in 30 cc of hot distilled water. Twenty grams of a commercial acid-form ZSM-5 zeolite were impregnated with the solution at room temperature for 3 hrs. After drying overnight at 121.1° C. (250° F.) the impregnated zeolite was calcined in air at a temperature of 593° C. (1100° F.), for 8 hours. The resultant catalyst was determined to contain 3.8, 2, and 0.4 percent respectively of chromium, molybdenum and phosphorus.

Catalyst B was prepared by dissolving two grams of ammonium molybdate, $(NH_4)_2MO_4$, 0.24 grams of phosphoric acid $(H_3PO_4)$ and 3.1 grams of cobalt nitrate, $Co(NO_3)_2.6H_2O$, in 20 cc of hot water. Twenty (20) grams of commercial acid-form ZSM-5 catalyst was impregnated at room temperature for 3 hours with this solution dried overnight at 250° F., and then heated in air at 1100° F. for 8 hours.

Catalyst C was prepared by dissolving 11.5 grams of zinc nitrate, $Zn(NO_3)_2.6H_2O$, and 3.8 grams of chromic nitrate, $Cr(NO_3)_2.9H_2O$, in 60 cc of distilled water. Fifty (50) grams of commercial acid-form ZSM-5 were impregnated with this solution at room temperature for 4 hours. The impregnated catalyst was then dried overnight at 93.3° C. (200° F.) and subsequently heated first in a nitrogen atmosphere at 537.8° C. (1000° F.) for 1 hour and then for 1 hour in an air atmosphere at 593° C. (1100° F.).

Catalyst D was prepared by dissolving 11.5 grams of zinc nitrate, $Zn(NO_3)_2.6H_2O$, and 1.9 grams of copper nitrate, $Cu(NO_3)_2.3H_2O$, in distilled water. This solution was then impregnated on 50 grams of commercial acid-form ZSM-5 zeolite. The catalyst was then dried overnight at 250° F. and first heated in a nitrogen atmosphere at 537.8° C. (1000° F.) for 1 hour and then heated in an air atmosphere at 593° C. (1100° F.) for 3 hours.

Catalyst E was prepared by adding 2.4 grams of niobium oxalate, $Nb(HC_2O_4)_5$, to 70 cc of an aqueous solution containing 2.7 grams of ammonium para-molybdate and 1.2 grams of ammonium m-vanadate, $NH_4VO_3$. This solution was then impregnated on 40 grams of commercial acid-form ZSM-5. The impregnated zeolite catalyst was dried in an oven overnight at 121.1° C. (250° F.) and was then calcined at a temperature of 538° C. (1000° F.).

Catalyst F was prepared by making a physical mixture of zinc ferrite and acid form ZSM-5 zeolite. The zinc ferrite was prepared according to the disclosure of U.S. Pat. No. 3,937,748.

In Runs 2 to 7 each of the catalysts described above was tested by flowing an oxygen-propane mixture over the catalyst in a glass unit at atmospheric pressure. In addition, an oxygen-ethane mixture was also passed over Catalyst E in run 9. Runs 1 and 8 represent tests made with acid-form ZSM-5 zeolite catalyst without any added metal component.

5. The process of claim 4 wherein said alkali metal salt is sodium carbonate.

6. The process of claim 1 wherein said oxidative dehydrogenation catalyst comprises ferric oxide, potassium oxide, and chromium oxide.

7. The process of claim 1 wherein said oxidative dehydrogenation catalyst comprises iron ferrite and an oxide of a metal selected from the group consisting of cerium, zinc, manganese, lead, and mixtures thereof.

| | AROMATIZATION OF PROPANE AND ETHANE | | | | | | | | |
|---|---|---|---|---|---|---|---|---|---|
| Run No. | 1 | 2 | 3 | 4 | 5 | 6 | 7 | 8 | 9 |
| | | A | B | C | D | E | F | | E |
| Catalyst | HZSM-5 | Cr/Mo/P | Co/Mo/P | Zn/Cr | Zn/Cu | Nb/V/Mo | Zn/Fe | HZSM-5 | Nb/V/Mo |
| Conditions | | | | | | | | | |
| Temp, °C. | 566 | → | → | → | → | 593 | 510 | 566 | 593 |
| Pressure, pascal | $1 \times 10^5$ | → | → | → | → | → | → | → | → |
| WHSV | 1.9 | → | → | → | → | 1 | 1 | 1.2 | 0.5 |
| $O_2$ Conc in feed, wt percent | 20 | → | → | → | → | 24 | 24 | 20 | 30 |
| Time on stream, hrs. | 1 | 1.5 | 2 | 4 | 4 | 2 | 3 | 2 | 2 |
| Hydrocarbon Conversion* weight percent | 70 | 46 | 64 | 82 | 79 | 69 | 47 | 30 | 30 |
| Aromatics Yield, g/100g of hydrocarbon charged | 12 | 19 | 16 | 18 | 23 | 22 | 16 | 0.9 | 12 |
| Aromatics Selectivity, g/100g of hydrocarbon converted | 17 | 41 | 25 | 22 | 29 | 32 | 34 | 23 | 39 |
| percent increase in yield | — | 58 | 33 | 50 | 92 | 83 | 33 | — | 123 |
| percent increase in selectivity | — | 140 | 47 | 29 | 71 | 88 | 100 | — | 160 |
| Prod. Analysis (wt. percent) | | | | | | | | | |
| $H_2$ | 0.4 | 0.5 | 1.1 | 3.1 | 3.1 | 1.5 | 1.6 | 0 | 1.4 |
| CO | 12.2 | 6.1 | 13.2 | 15.4 | 13.3 | 14.7 | 11.2 | 13.3 | 14.3 |
| $CO_2$ | 0.8 | 0.1 | 2.5 | 10.5 | 9.8 | 1.7 | 10.1 | 9.7 | 4.6 |
| $O_2$ | 0 | 0.6 | 2.4 | 0.7 | 0.7 | 3.1 | 2.1 | 0 | 0 |
| $H_2O$ | 21.3 | 13.7 | 14.6 | 5.9 | 4.7 | 13.9 | 8.9 | 22.6 | 10.1 |
| $C_1$ | 9.2 | 5.8 | 9.4 | 17.5 | 16.3 | 9.0 | 5.8 | 0.2 | 6.3 |
| $C_2=$ | 7.9 | 6.0 | 5.4 | 1.7 | 1.8 | 6.0 | 1.4 | 2.5 | 4.6 |
| $C_2°$ | 4.4 | 1.7 | 4.1 | 11.5 | 11.6 | 5.9 | 1.9 | 50.0 | 48.6 |
| $C_3=$ | 6.3 | 4.9 | 4.2 | 3.2 | 3.7 | 2.5 | 1.3 | 0.4 | 0.8 |
| $C_3°$ | 24.1 | 42.8 | 29.0 | 14.8 | 16.6 | 23.6 | 42.1 | 0.4 | 0.7 |
| $C_4$ | 3.1 | 1.6 | 1.3 | 0.3 | 0.1 | 0.9 | 0.4 | 0 | 0 |
| $C_5 + C_6$ | 0.4 | 0 | 0.1 | 0.8 | 0 | 0.4 | 0.0 | 0 | 0 |
| Benzene | 2.6 | 4.6 | 4.4 | 7.0 | 8.4 | 4.1 | 4.9 | 0.4 | 4.5 |
| Toluene | 4.8 | 5.3 | 5.3 | 5.2 | 6.7 | 6.9 | 5.4 | 0.2 | 3.0 |
| Ethyl benzene | 0.1 | 0.3 | 0.2 | 0.1 | 0.2 | 0.7 | 0.2 | 0 | 0.2 |
| Xylenes | 1.9 | 3.8 | 1.9 | 1.8 | 2.3 | 4.9 | 2.6 | 0.1 | 0.7 |
| $C_9+$ | 0.1 | 1.2 | 0.6 | 0.4 | 0.5 | 0.5 | 0.1 | 0 | 0.1 |
| Total | 99.6 | 99.0 | 99.7 | 99.9 | 99.8 | 100 | 100 | 99.8 | 99.9 |

*In Runs 1-7 feedstock was propane.
In Runs 8 and 9 ethane was the feedstock.

What is claimed is:

1. A process for producing aromatics from a feedstock containing predominantly paraffinic hydrocarbons of 2 to 16 carbon atoms which comprises contacting said feedstock and air or oxygen with a crystalline zeolite catalyst comprising a zeolite having a constraint index within the approximate range of 1 to 12 and a silica to alumina ratio of at least 12 and having incorporated therein a minor amount of metal or metal oxide oxidative dehydrogenation components.

2. The process of claim 1 wherein the temperature of said contacting is between about 450° and about 650° C.

3. The process of claim 1 wherein said oxidative dehydrogenation catalyst is iron oxide.

4. The process of claim 3 wherein said iron oxide oxidative dehydrogenation catalyst is promoted with an alkali metal salt.

8. The process of claim 1 wherein said oxidative dehydrogenation catalyst comprises a mixture of the oxides of cobalt, molybdenum, and chromium.

9. The process of claim 1 wherein said oxidative dehydrogenation catalyst comprises a mixture of the oxides of zinc, molybdenum and chromium.

10. The process of claim 1 wherein said oxidative dehydrogenation catalyst is a mixture of oxides of chromium and molybdenum.

11. The process of claim 10 wherein said oxidative dehydrogenation catalyst contains phosphorous.

12. The process of claim 10 wherein said oxidative dehydrogenation catalyst contains one or more metals selected from the group consisting of metals from groups IA, IIA, IVB and VIII of the periodic table.

13. The process of claim 1 wherein said oxidative dehydrogenation catalyst comprises a mixture of the oxides of niobium, vanadium and molybdenum.

14. The process of claim 1 wherein said zeolite is selected from the group consisting of ZSM-5, ZSM-11, ZSM-12, ZSM-23, ZSM-35, ZSM-38 and ZSM-48.

15. The process of claim 1 wherein said process is carried out at a pressure of between about $1.01 \times 10^5$ to about $42.38 \times 10^5$ pascal.

16. The process of claim 2 wherein the molar ratio of oxygen to the total moles of $C_2$ to $C_{16}$ hydrocarbons in the paraffinic feedstock is between about 0.1 and about 1.

17. The process of claim 1 wherein said feedstock is predominantly ethane.

18. The process of claim 1 wherein said feedstock is predominantly propane.

19. The process of claim 1 wherein said process is carried out at a pressure of about $1.01 \times 10^5$ to about $21.69 \times 10^5$ pascal.

* * * * *